United States Patent [19]
Strowe

[11] Patent Number: 5,992,899
[45] Date of Patent: Nov. 30, 1999

[54] ADAPTER FOR MOUNTING A FLUID HANDLING DEVICE ON A CATHETER TUBING

[75] Inventor: Robert J. Strowe, Ramsey, N.J.

[73] Assignee: Becton, Dickinson and Company, Franklin Lakes, N.J.

[21] Appl. No.: 08/932,234

[22] Filed: Sep. 17, 1997

[51] Int. Cl.⁶ .............................. F16L 37/04; A61M 5/178
[52] U.S. Cl. ............................ 285/93; 285/346; 285/338; 604/283; 604/256
[58] Field of Search ............................. 285/93, 338, 346; 604/283, 256

[56] References Cited

U.S. PATENT DOCUMENTS

| | | | |
|---|---|---|---|
| 3,876,234 | 4/1975 | Harms | 285/38 |
| 4,613,329 | 9/1986 | Bodicky | 604/158 |
| 4,834,719 | 5/1989 | Arenas | 604/243 |
| 5,053,015 | 10/1991 | Gross | 604/167 |
| 5,226,898 | 7/1993 | Gross | 604/243 |
| 5,279,597 | 1/1994 | Dassa et al. | 604/283 |
| 5,338,313 | 8/1994 | Mollenauer et al. | 604/283 |
| 5,397,310 | 3/1995 | Chu et al. | 604/158 |
| 5,464,400 | 11/1995 | Collins | 604/283 |
| 5,591,137 | 1/1997 | Stevens | 604/283 |
| 5,820,601 | 10/1998 | Mayer | 604/167 |

FOREIGN PATENT DOCUMENTS

| | | |
|---|---|---|
| 0 856 332 A1 | 8/1998 | European Pat. Off. |
| 2072288 | 9/1981 | United Kingdom. |

*Primary Examiner*—Eric K. Nicholson
*Attorney, Agent, or Firm*—Arthur D. Dawson; Scott S. Servilla

[57] ABSTRACT

An adapter for attaching a fluid handling device to a catheter tubing includes a body with a proximal end, a distal end and a passageway therethrough. The body has a proximal end that has a fitting for attaching a fluid handling device. The distal end of the body includes an elongate receptacle with an inside surface that has least one engagement lug. There is an elongate resilient member disposed within the receptacle with a first end and a second end and a coaxial passage therethrough. The passage has an inside diameter to accept and form a releasable substantially fluid tight connection to a preselected catheter tube. The resilient member has a first conjugate engagement to the receptacle engagement lug at the first end and a second engagement at the second end. The adapter also has a latch member disposed over the receptacle to contain the resilient member that has a distal axial access port therein to receive the catheter tube into the resilient member passage. The latch member has an inside surface with at least one second engagement lug for engaging the second end engagement of the resilient member. The latch member is disposed for rotatable movement with respect to the body between an insertion position and a latched position. The rotation of the latch member with respect to the body rotationally displaces the first end of the resilient member with respect to the second end of the resilient member, thereby decreasing the inside diameter of the resilient member passage.

18 Claims, 8 Drawing Sheets

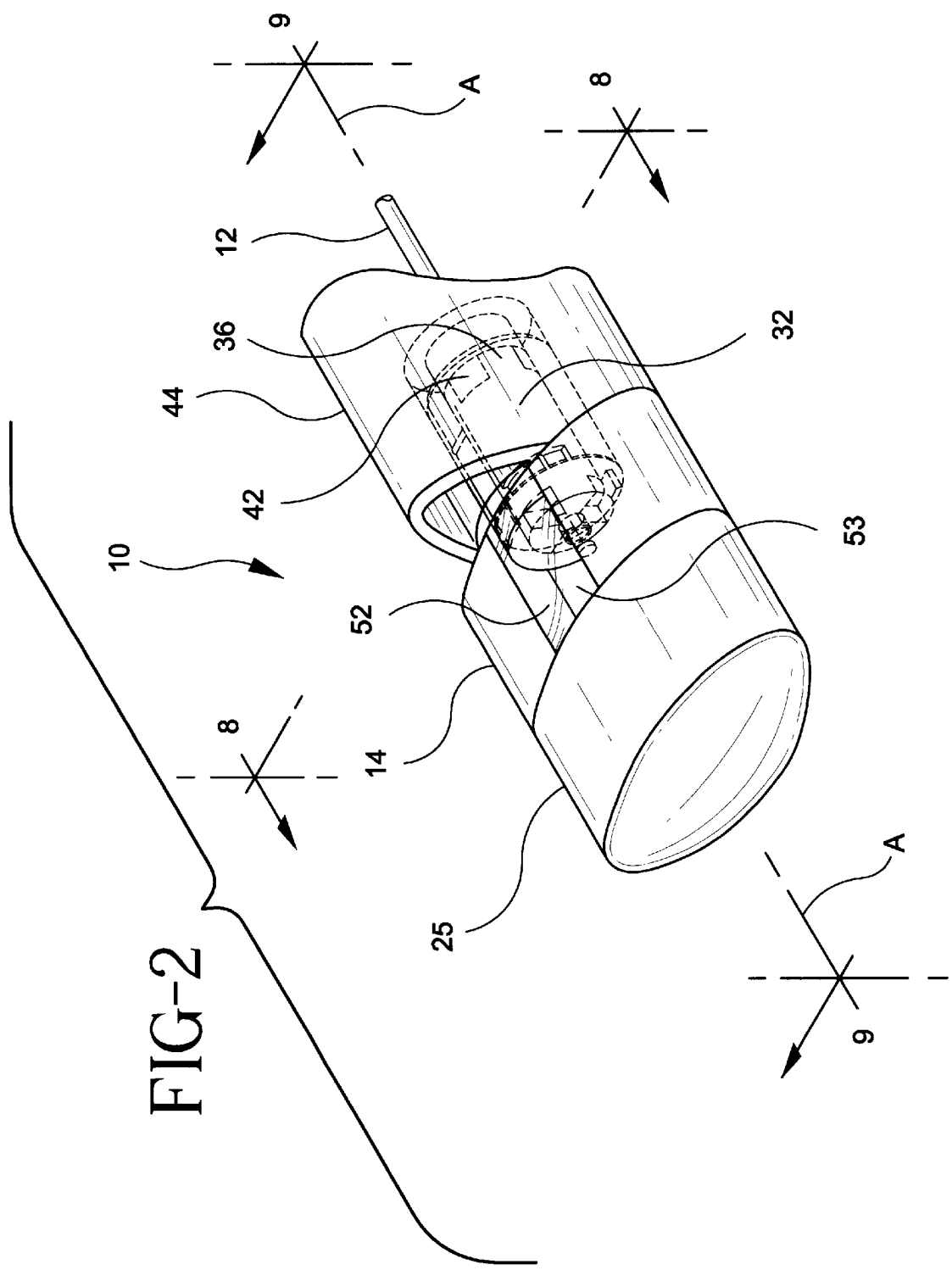

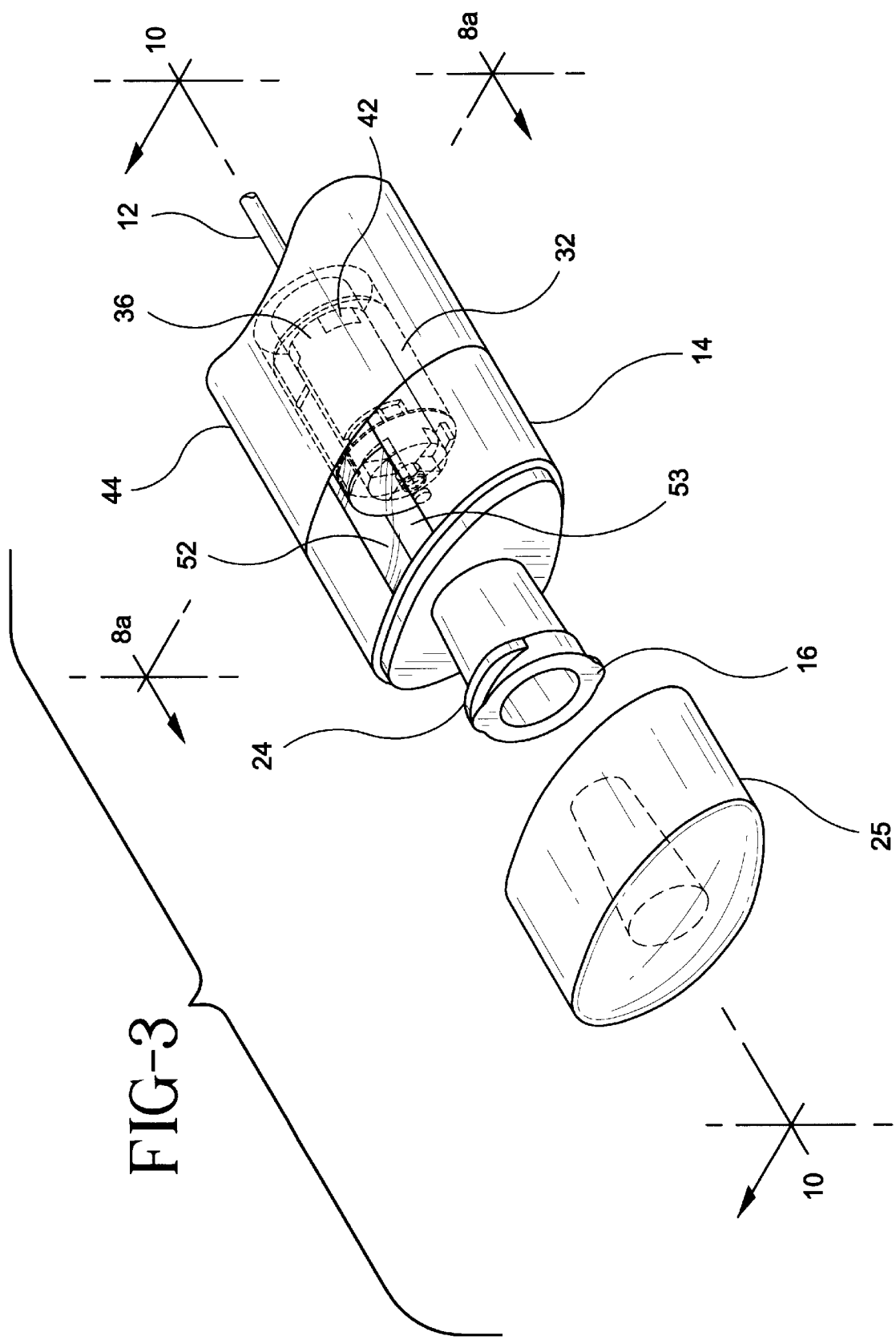

ADAPTER FOR MOUNTING A FLUID HANDLING DEVICE ON A CATHETER TUBING

FIELD OF THE INVENTION

The present invention is generally related to the field of catheters and more particularly to adapters for mounting a fluid handling device on a catheter tubing.

BACKGROUND

Catheters are elongate hollow tubes that are used to transmit fluids into or out of the body of a patient. Conventions followed for the devices described in this disclosure are that the term "proximal" is the direction away from the patient and toward the practitioner and the term "distal" refers to the direction toward the patient and away from the practitioner. There are many types of catheters currently used in medical practice. Some catheters are sufficiently strong and rigid to be introduced by themselves, urinary catheters are examples of this type of catheter. Another catheter type is positioned on the outside of a sharp introducer needle and slid down over the needle into the patient's body using the needle to make the penetration and provide a guide to placement of the catheter, many intravenous catheters are of this type. This disclosure is related to yet another type, a catheter that is introduced into the patient through the bore of a sharp introducer needle. Through-the-needle catheters are further separated into two types by the introducer needle. When a through-the-needle catheter has a fixed hub for attachment of a fluid handling device, the introducer needle cannot be slid off the proximal end of the catheter. Catheters with fixed hubs either are used with a splittable introducer needle or the needle must be left on the catheter. One important application of catheters in medical practice is the use of long flexible catheters to introduce medicaments, often anesthetic or analgesic formulations, into the spine of a patient. In this application, the long (50–75 cm) flexible catheter tubing (generally 19–21 gauge) is introduced into the patient's epidural space through the bore of an introducer needle.

These spinal anesthesia procedures are widely used in hospital practice, with the generic name of "an epidural." As an example, the use of an epidural anesthetic is described in obstetric practice. The epidural anesthetic procedure is useful in many other type of procedures. In a typical obstetric procedure, the epidural catheter is often placed early in the patient's labor with the patient lying on her side, then the patient is placed on her back with the knees elevated for the rest of the delivery. Since the patient is on her back, the introducer needle generally must be removed. Most epidural catheters do not have fixed hubs thus allowing the introducer needle to be slid proximally off of the catheter and removed. Once the needle is removed, it is necessary to mount an adapter onto the catheter so that a fluid handling device such as a syringe may be attached to the catheter. The adapter is then often secured with tape onto the patient's body. The Tuohy-Borst adapter was developed for this application. The Tuohy-Borst adapter allows a fluid handling device with a male luer fitting to be mounted onto a small diameter (generally 19–21 gauge: Nominal Outside Diameters for these 19 to 21 gauges are between about 1.10 mm [19 gauge] to about 0.8 mm [21 gauge]) flexible catheter tube. The original Tuohy-Borst adapter is formed from metal and is considered reusable. Other variants of the original Tuohy-Borst are now available formed from thermoplastics. The thermoplastic adapters are generally supplied sterile and are considered single-use and disposable. The Tuohy-Borst type adapters all depend in some degree on a threaded collar being screwed down around the catheter to compress a resilient plug contained in a body portion. The seal around the catheter is formed by compressing the tip of the resilient plug into a cavity around the catheter tube by screwing the collar down onto the plug. In most of these adapters, it is easy for a practitioner to inadvertently over-tighten the threaded collar and occlude the catheter lumen. Alternatively, if the collar is not tightened down sufficiently, the adapter may leak or may even come off of the catheter tube. Most of the available adapters are generally cylindrical, may include a releasable latch mechanism and require at least about one-half rotation of the collar portion with respect to the body portion to secure the adapter onto the catheter.

A widely used adapter, available from B. Braun, Bethlehem, Pa., has a collar and a body portion. The Braun adapter is capable of almost four complete rotations of the collar with respect to the body portion from the initial engagement of the threads. Additionally, if this collar of the B. Braun adapter is fully unthreaded from the body portion, it may detach and allow disassembly of the adapter. Another widely used adapter is the disposable successor to the reusable Tuohy-Borst available from Becton Dickinson and Company, Franklin Lakes, N.J. The collar of this successor adapter is fully seated on the body after only about two and one half rotations of the collar with respect to the body. Additionally, unlike the B. Braun adapter, the collar is retained on the body when completely unthreaded so that it cannot easily fall off Another available adapter, as disclosed in U.S. Pat. Nos. 5,053,015 and 5,226,898, has an external ratchet and includes small wings on both the body and the collar to facilitate the practitioners handling and, when the wings are aligned, provides some indication that the adapter is secured onto the tubing. When the adapter disclosed in the referenced patents is secured to the patient's body, the small wings may cause discomfort to the patient, and additionally, the adapter may sometimes be difficult for a gloved practitioner to handle.

Other than the catheter adapters disclosed in U.S. Pat. Nos. 5,053,015 and 5,226,898, substantially all of the available adapters do not provide the practitioner with much indication of the sufficiency of the degree of tightness of the collar with respect to the body, and it is not easily visually apparent if the collars are loosened so that the catheter tubing may be inserted into the adapter or if the collar is partially screwed down on the body, making it difficult to insert the catheter tube into the adapter body. Operating room time is expensive, and additionally, many procedures are conducted under time constraints that potentially have impact on the patient's well being. As a result, practitioners and their support staff make every effort to set up repeatable procedures with standardized placements of equipment to facilitate rapid implementation of procedures. If a practitioner attempts to put an adapter onto a catheter tube and has difficulty because the adapter is partially threaded, additional time is required. If a practitioner inadvertently over-tightens a collar of an adapter occluding the lumen, he may believe the catheter is clogged or kinked, remove it and have to repeat the placement. The repeat procedure not only subjects the patient to additional risk, but also significantly increases the time required. If an adapter is not sufficiently tightened, it may fall off or leak during an extended procedure, thereby resulting in improper patient medication. If a gloved practitioner has difficulty handling an adapter and drops it, there may be a time delay while another adapter is procured, and, in the case where the adapter is part of a procedure kit, another whole kit, with a significant cost increment, may need to be opened just to obtain another adapter.

If a catheter adapter that was easily handled by a gloved practitioner was available that provided the practitioner with a positive indication of its status, i.e., ready-to-receive a catheter tube or fully tightened; that could not be overtightened; and required only about one quarter turn of the collar with respect to the body to be fully tightened, the art of catheter adapters would be advanced. Such a catheter adapter is disclosed below.

SUMMARY

An adapter of the present invention for attaching a fluid handling device to a catheter tubing includes a body with a proximal end, a distal end and a passageway therethrough that defines a longitudinal axis. The body has a proximal end that has a fitting for attaching a fluid handling device. The distal end of the body includes an inside surface. The adapter also includes an elongate resilient member that has a first end and a second end with a coaxial passage therethrough. The passage has an inside diameter suitable to accept and to form a releasable substantially fluid tight connection to a preselected catheter tube of a preselected outside diameter. The resilient member has an attachment at the first end to the inside surface of the body. The adapter also has a latch member disposed over the resilient member, with a distal axial access port therein for fitment of a proximal end of the catheter tube into the resilient member passage. The latch member has an inside surface attached to the second end of the resilient member. The latch member is disposed for rotatable movement with respect to the body between an insertion position wherein the passage in the resilient member is accessible to the catheter and the inside diameter of the resilient member passage is sufficient to accept the outside diameter of the catheter and a latched position wherein the inside diameter of the resilient member passage is smaller than the outside diameter of the catheter to retain the catheter in the receptacle. The rotation of the latch member with respect to the body between the insertion position and the latched position rotationally displaces the first end of the resilient member with respect to the second end of the resilient member, thereby decreasing the inside diameter at least a portion of the resilient member passage.

The catheter adapter of the invention provides a practitioner with an easy-to-use adapter that is readily fitted onto a catheter tube. The invention provides the practitioner with positive indications that the adapter is ready to receive the catheter, as well as when the catheter is properly positioned in the adapter, and when the adapter is fully engaged to retain the catheter. Since the adapter of the invention requires only one-quarter turn to engage the cathteter, the adapter of the invention is unlikely to be overtightened and occlude the catheter. Further, the cathteter adapter of the invention is more easily handled by a gloved practitioner than the mostly cylindrical adapters currently available.

BRIEF DESCRIPTION OF THE DRAWINGS

FIG. 2 is a partial schematic perspective of the adapter of FIG. 1 in the unlatched positions;

FIG. 3 is a partial schematic perspective view of the adapter of FIG. 1 in the latched position;

FIG. 8a is a schematic horizontal cross-sectional view of the resilient member of the invention of FIG. 3 taken from FIG. 3 along the line 8a—8a;

DETAILED DESCRIPTION

Figure 1:
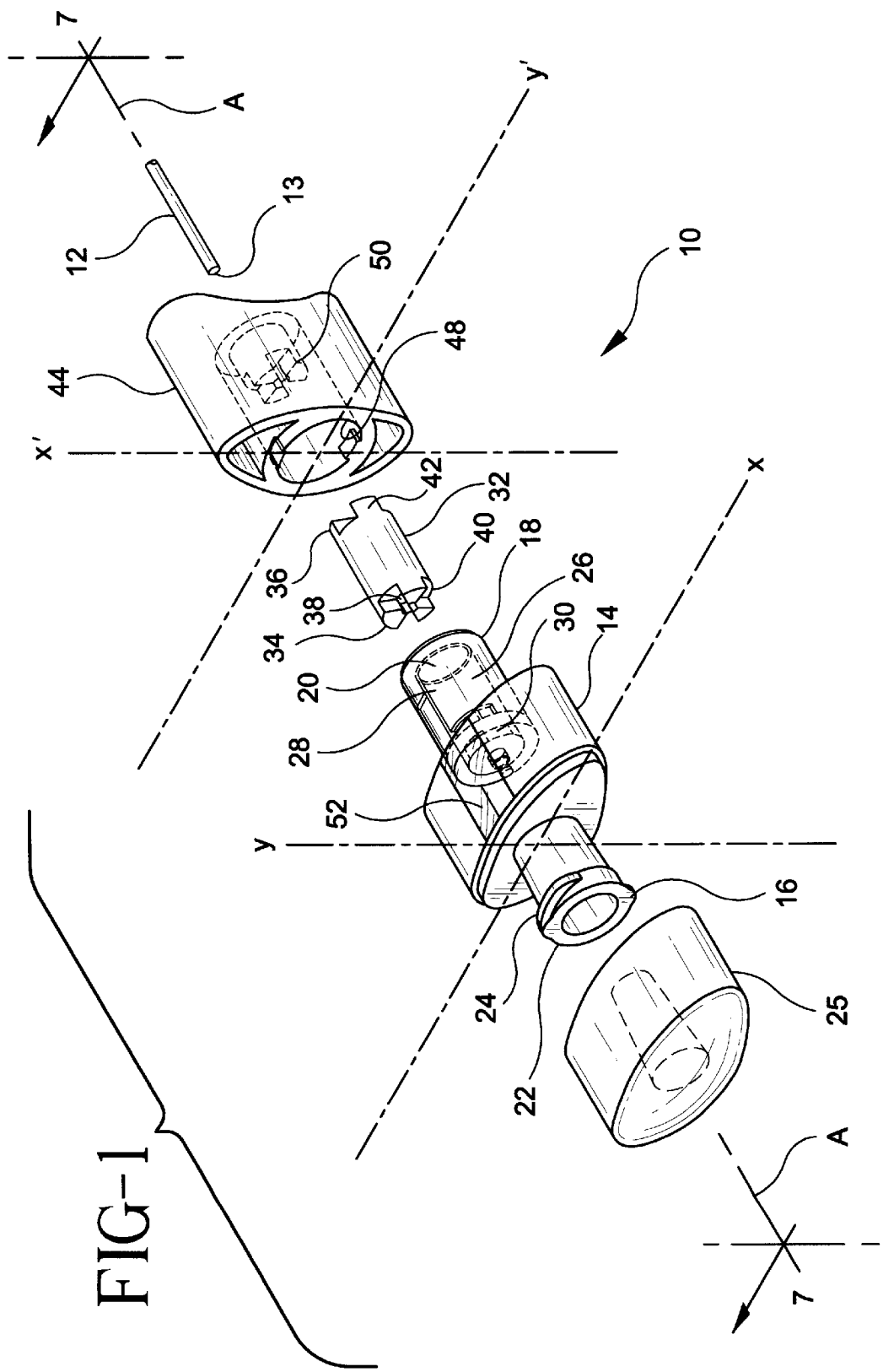
FIG. 1 is an exploded perspective view of the catheter adapter of the invention.
Figures 5, 6:
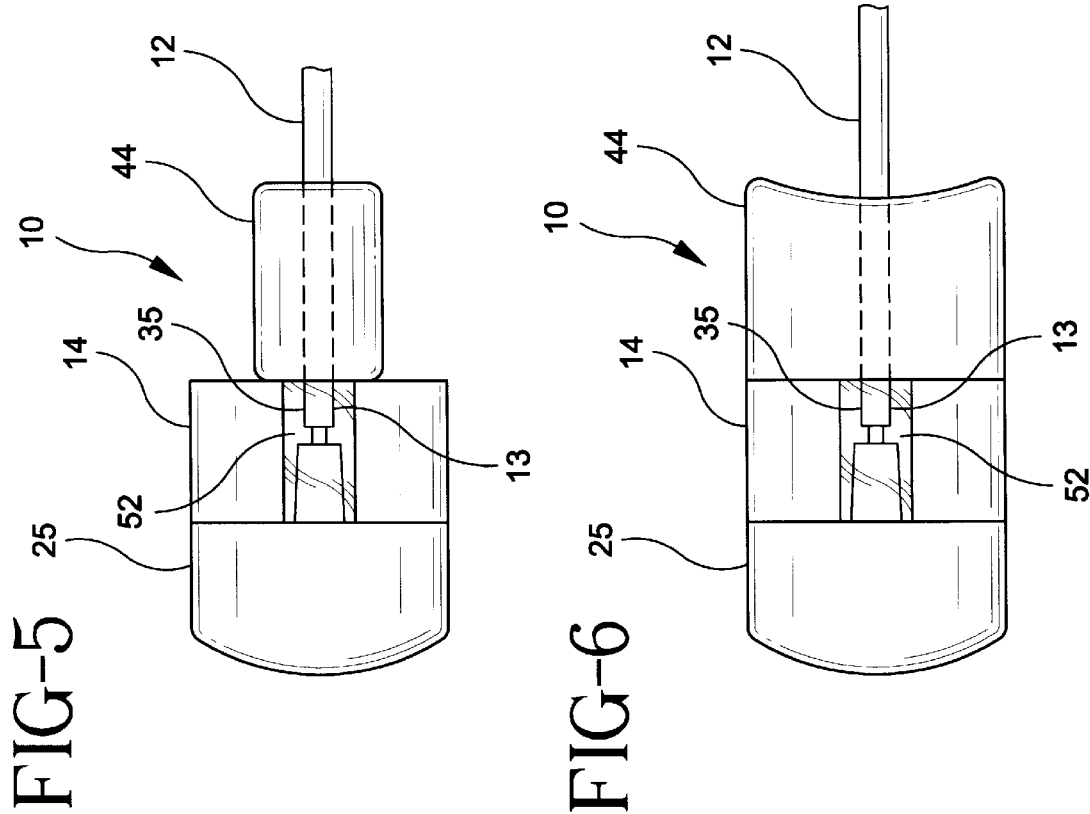
FIG. 5 is a schematic top plan view of the invention of FIG. 1 in the unlatched position.
FIG. 6 is a schematic top plan view of the invention of FIG. 1 in the latched position.

While this invention is satisfied by embodiments in many different forms, there are shown in the drawings and herein described in detail, embodiments of the invention with the understanding that the present disclosure is to be considered as exemplary of the principles of the present invention and is not intended to limit the scope of the invention to the embodiments illustrated. The scope of the invention is measured by the appended claims and their equivalents. In this disclosure, the term "proximal" refers to the portions of the device closest to the practitioner and the term "distal" refers to the portion of the device away from the practitioner.

Referring to FIGS. 1–10, an adapter 10 of the present invention useful for attaching a fluid handling device to a catheter tubing 12 includes a body 14 with a proximal end 16, a distal end 18 and a passageway 20 therethrough that defines a longitudinal axis "A". Proximal end 16 has a fitting 22, preferably a female luer fitting 24, for attaching the fluid handling device. Distal end 18 of the body preferably includes an elongate receptacle 26 with an inside surface 28 that has least one engagement lug 30. Adapter 10 also includes an elongate resilient member 32 disposed within receptacle 26 that has a first end 34 and a second end 36 with a preferably coaxial passage 38 therethrough. Passage 38 has an inside diameter "h" to accept and to form a releasable substantially fluid tight connection to preselected catheter tube 12 of a preselected outside diameter "d". Resilient member 32 preferably has a first conjugate engagement 40 to receptacle engagement lug 30 at first end 34 and a second engagement 42 at second end 36. Adapter 10 also has a latch member 44 disposed over receptacle 26 to contain the resilient member. Latch member 44 has a distal axial access port 46 therein for fitment of a proximal end 13 of catheter tube 12 into resilient member passage 38. Latch member 44 preferably has an inside surface 48 with at least one second engagement lug 50 for engaging second end engagement 42 of resilient member 32. Alternatively, resilient member 32 may be fixedly attached to body 14 and latch member 44 by adhesive bonds or the like. Latch member 44 is disposed for rotatable movement with respect to body 14 between an insertion position, best seen in FIGS. 1, 7 and 9, and a latched position best seen in FIGS. 3 and 10. In the insertion position, passage 38 in resilient member 32 is accessible to catheter 12 and, referring to FIG. 8, inside diameter "h" of resilient member passage 38 is sufficient to allow placement of catheter 12 with outside diameter "d" inside passage 38r. In the latched position, inside diameter "h" of resilient member passage 38 is smaller than outside diameter "d" of the catheter to retain the catheter in the receptacle. The rotation of latch member 44 with respect to body 14 between the insertion position and the latched position rotationally displaces first end 34 of resilient member 32 with respect to second end 36 of the resilient member, thereby decreasing inside diameter "h" of at least a portion of resilient member passage 38.

Referring to FIG. 1, first end 34 of resilient member 32 preferably has three conjugate engagements 40 to engage three engagement lugs 30 on inside surface 28 of receptacle 26 of body 14. Additionally, second end 36 resilient member 32 preferably has three conjugate second end engagements 42 to engage three engagement lugs 50 on inside surface 48 of latch member 44. For particular applications, the number of conjugate engagements on either end of resilient member 32 may be the same or different to correspond to the number of engagement lugs on the body and the latch member. The preferred three conjugate engagements and lugs configuration of the adapter provides a substantially uniform torque to the resilient member when the latch member is rotated with respect to the body.

Figure 4:
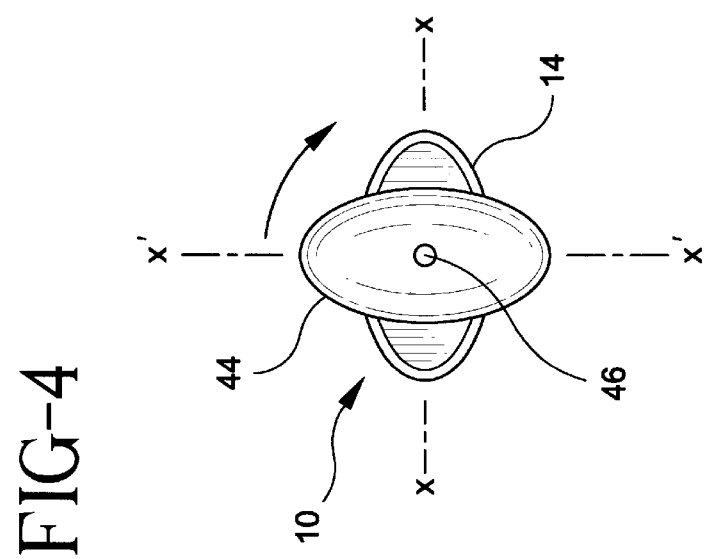
FIG. 4 is a plan view of the invention of FIG. 1 from the distal end.
Figure 8A:
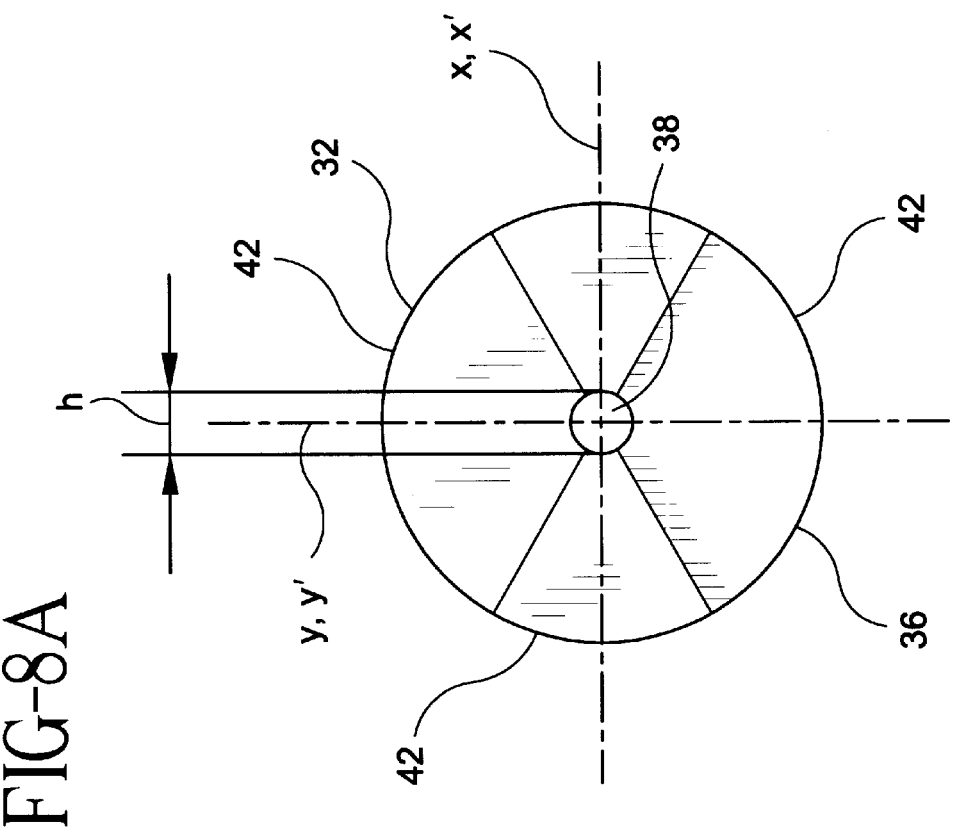
Figure 8:
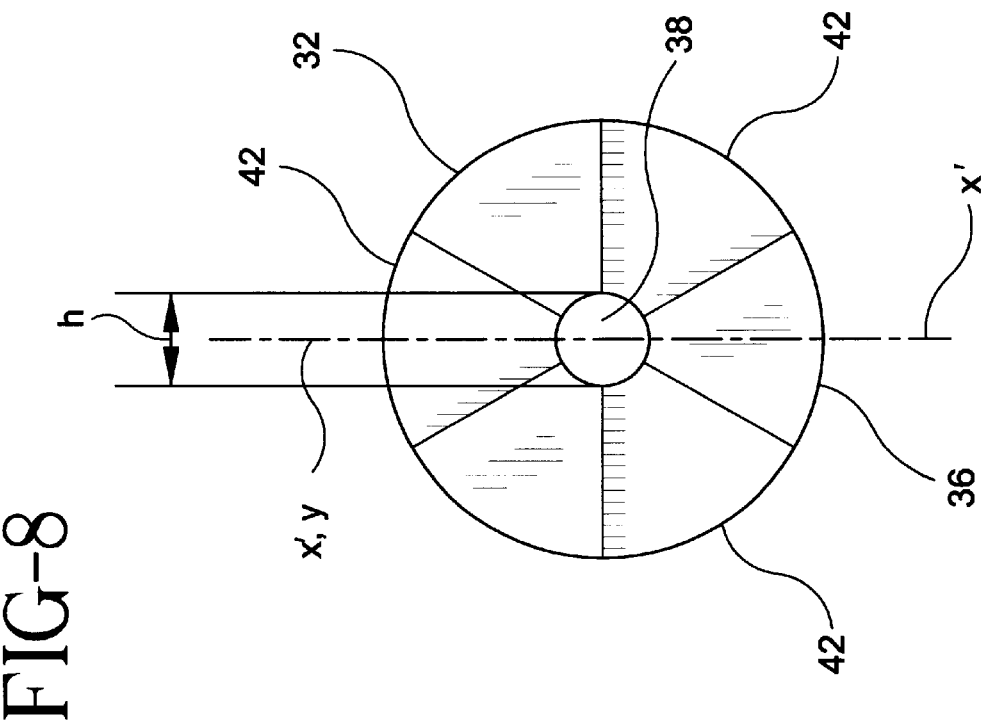
FIG. 8 is a schematic horizontal cross-sectional view of the resilient member of the invention of FIG. 2 taken from FIG. 2 along the line 8—8.
Figure 9:
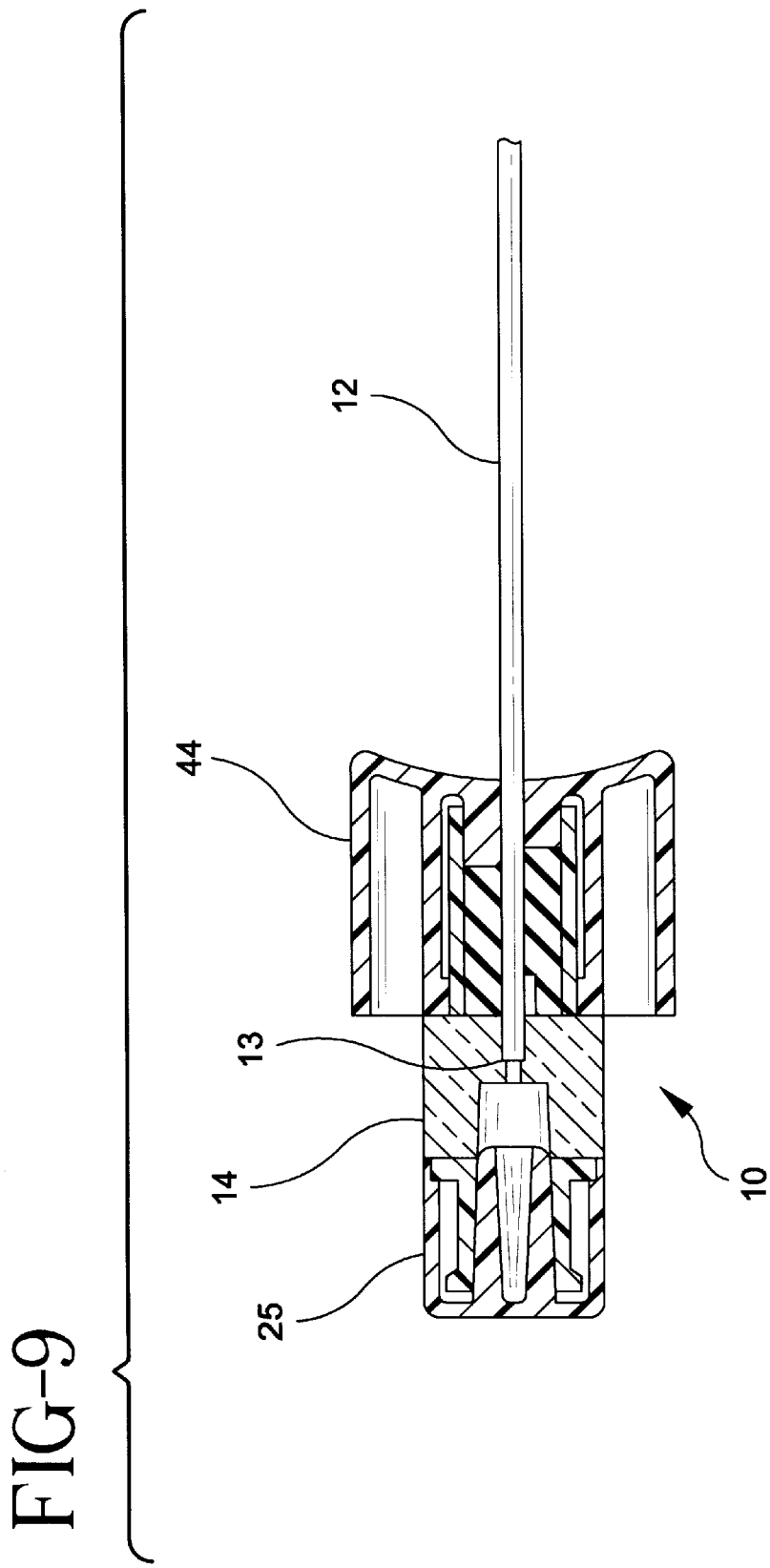
FIG. 9 is a longitudinal cross-sectional view of the invention of FIG. 1 taken from FIG. 2 along the line 9—9.
Figure 10:
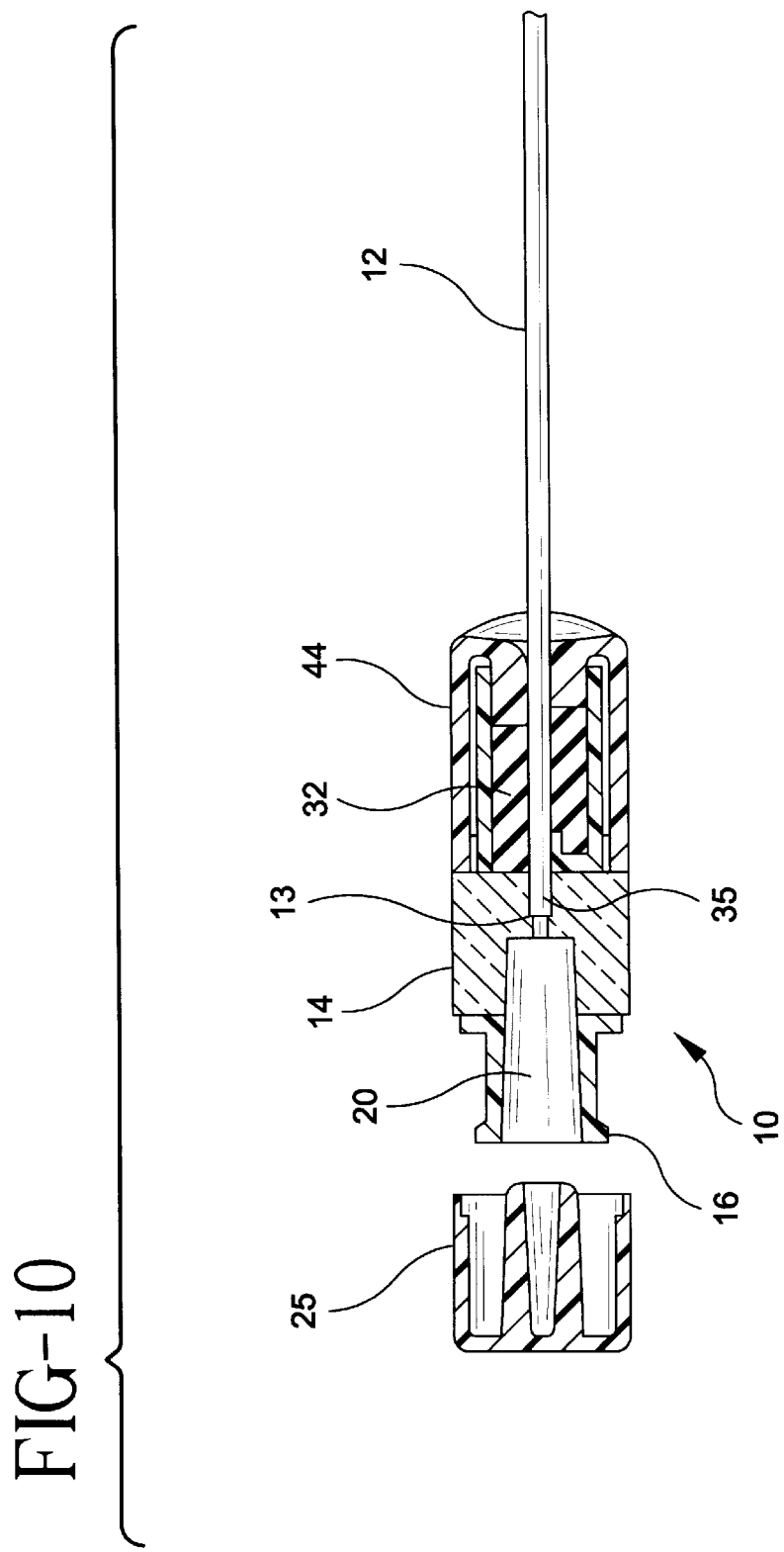
FIG. 10 is a longitudinal cross-sectional view of the invention of FIG. 1 taken from FIG. 3 along the line 10—10.

As shown in FIG. 1, latch member 44 and body 14 are preferably each formed in shape of an elongate tube with substantially identical elliptical cross-sections, each shape having a long axis "x, x'", respectively, and a short axis "y, y'", respectively, and disposed so that when latch member 44 is in the latched position with respect to body 14, as seen in FIG. 3, long axes x, x' and short axes y, y' are substantially aligned and when latch member 44 is in the insertion position as seen in FIG. 1, short axis y of body 14 is substantially aligned with long axis x' of latch member 44 with long axis x of the body being substantially aligned with short axis y' of latch member 44 thereby providing a visual and tactile indication of the position of latch member 44 with respect to body 14 and leverage to facilitate the practitioner's rotatable movement of latch member 44 with respect to body 14. FIG. 4, provides a schematic illustration of the relationship of the body "x" axis to the latch member "x'" axis as the latch member is moved from the insertion position to the latched position. FIGS. 8 and 8a schematically illustrate the effect of the rotation on resilient member 32 as latch member 44 is rotated with respect to body 14 with the resultant reduction in diameter "h" of passage 38. Many other shapes having asymmetric cross-sections, in addition to the preferred elliptical shape, for adapter 10 may be envisioned and are considered to be within the scope of the invention.

The preferred elliptical shape favors a preferred rotation of about ninety degrees for the rotation of the latch member with respect to the body. Preferably, inside diameter "h" of the resilient member passage 38 is selected to allow free placement of a preselected catheter 12 with outside diameter "d" when adapter 10 is in the insertion position and inside diameter "h" is reduced to form a substantially fluid tight seal about catheter 12 outside diameter "d" when the latch member is rotated to the latched position. The reduction of inside diameter "h" by rotation of second end 36 with respect to first end 34 applies a substantially uniform grasping force to the outside surface of the catheter. The result of this uniform force application to the catheter is secure retention of the catheter with a substantially lower risk of occlusion of the catheter than with the previously disclosed catheter adapters. The previously disclosed adapters generally depend upon compression of the first end of a resilient member against a conical or similar catheter seat thus applying the retention force to only a small portion of the catheter. Additionally, since many of the previously disclosed catheter adapters are capable of several complete rotations of the attachment nut with respect to the body there is a much greater probability of overtightening the adapter with concomitant occlusion of the catheter than with the adapter of the invention.

Figure 7:
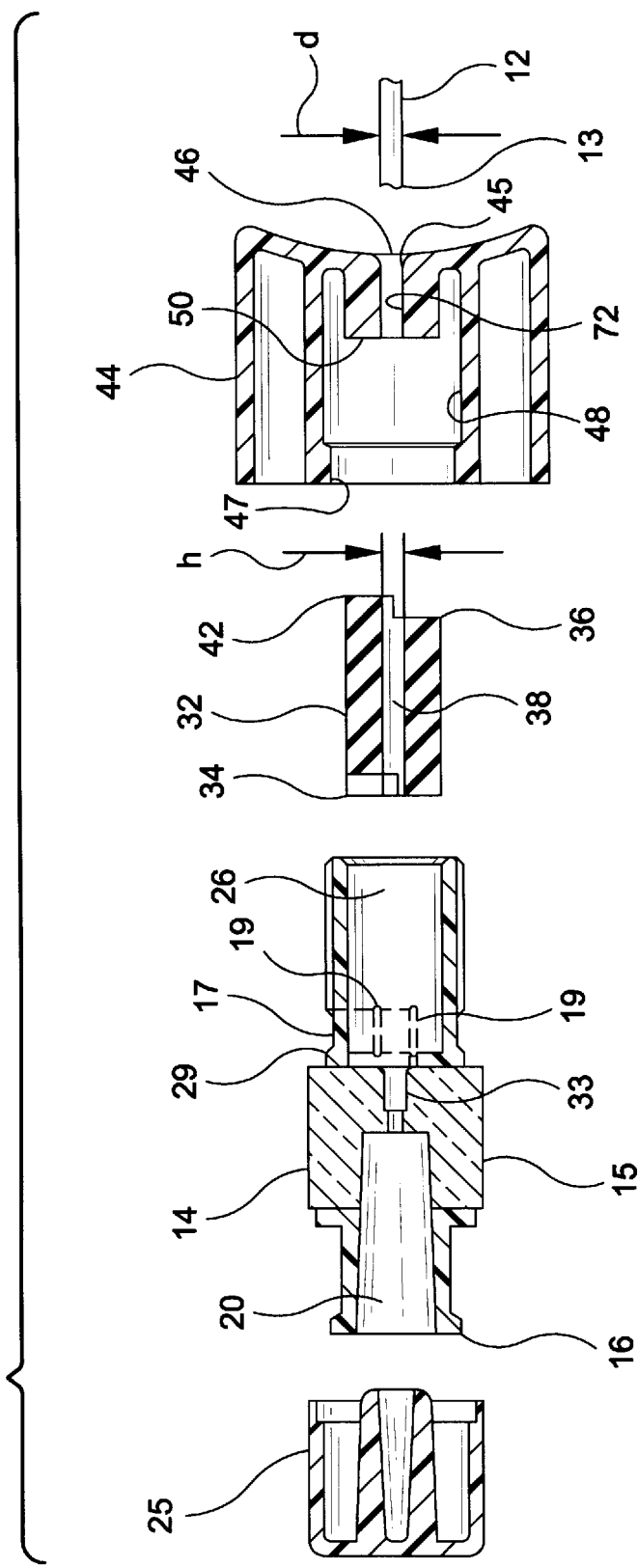
FIG. 7 is a longitudinal cross-sectional view of the invention of FIG. 1 taken along the line 7—7.

As is best seen in FIG. 7, an outside surface 15 of body 14 includes a channel 17 disposed to interact with a shoulder 47 on inside surface 48 of latch member 44. When latch member 44 is mounted on body 14, shoulder 47 is positioned in channel 17 and serves to retain latch member 44 on body 14. Channel 17 and shoulder 47 also serve to direct the rotation of latch member 44 with respect to body 14 in a cam/cam follower relation. Preferably, channel 17 further includes bumps 19 to provide a tactile and audible snap as latch member 44 is rotated with respect to body 44 between the insertion position and the latched position to provide the practitioner with a positive indication that adapter 10 is in the insertion position and the latched position.

Receptacle 26 is generally coaxial with passageway 20 and has a closed bottom 29 defining a catheter seat 31 for fluidly connecting catheter 12 to proximal fitting 22. Catheter seat 31 includes an axial recess 33 therein that has an axial opening 35 in closed bottom 29 of receptacle 26. Recess 33 is sized to receive a proximal end 13 of the catheter.

While the outside surface of the body and the latch member may have a textured surface to facilitate handling by a gloved practitioner, preferably, as seen in FIGS. 2, 3, 5 and 6, at least a portion of body 14 has a substantially transparent viewing area 52 so that when the proximal end 13 of the catheter is properly positioned in recess 33 of catheter seat 31 with catheter 12 substantially aligned with opening 35, proximal end 13 of the catheter is visible to the practitioner through area 52. Additionally, transparent viewing area 52 is preferably formed into a shape 53, such as a cylinder lens or any other shape to provide an enlarged image of recess 33, thereby enhancing the practitioner's visualization of proper placement of the catheter.

The preferred limitation of one quarter turn to complete the movement between the latched and the unlatched position makes over-tightening with concomitant occlusion of the catheter lumen substantially less likely than current adapters with a threaded fitting or ratcheted fitting that requires an indeterminate amount of rotation of the collar with respect to the body to achieve catheter retention. Additionally, with the adapter of the invention, it is readily apparent to the practitioner whether the adapter is latched or unlatched. Most current adapters do not provide an indication if they are sufficiently tightened or not, and, if the adapter is not tightened sufficiently, the catheter may leak or become dislodged from the adapter.

An additional benefit of the preferred elongate elliptical shape for the adapter of the invention is that the preferred shape is less likely than the currently available adapters to cause discomfort to the patient by being pressed into the patient's flesh while providing an enlarged surface area for the practitioner to apply tape for securing the adapter to the patient. Adapter 10 of the invention is substantially easier for a gloved practitioner to handle than most currently available adapters because of the preferred elongate elliptical shape.

Referring to FIGS. 1, 2 and 3, proximal end 16 with preferred female luer fitting 24 is preferably supplied with a removable cap 25 to protect the female luer fitting from contamination until the practitioner is ready to attach a fluid handling device. Preferably, removable cap 25 is shaped to correspond to the shape of body 14 and latch member 44.

Preferably, as best seen in FIG. 7, distal access port 46 provides that a force for inserting preselected catheter tube 12 into adapter 10 is less than a force for withdrawal of catheter tube 12 from the adapter before latch member 44 is moved with respect to body 14, thereby substantially reducing inadvertent catheter tube withdrawal from the adapter prior to latching. Preferably this differential withdrawal force of the catheter is provided by having at least one inward projection 60 on an inside surface 45 of access port 46. Projection 72 is preferably disposed to facilitate proximal motion of catheter tube 12 and to provide a resistance to distal motion of catheter tube 12. Preferably, inside surface 45 of access port 46 preferably has two inward projections 72.

Resilient member 32 may be formed from either thermoform or thermoset elastomeric materials, including, but not limited to natural rubber, ethylene propylene dimer rubber (EPDM), styrene butadiene rubber (SBR), silastic rubber, polyurethane elastomer and the like that have a Shore A durometer preferably between about 30 and 80. Preferably resilient member 32 is formed from a latex free natural rubber.

Suitable materials for forming body 14 and latch member 44 include but are not limited to thermoplastic materials such as polyethylene, polypropylene, polycarbonate, polystryrene and the like. Preferably, at least body 14 is formed from a substantially transparent material to facilitate the practitioners observation of the placement of catheter 12 in recess 33 prior to rotation of latch member 44 with respect to body 14.

All of the materials selected to form adapter 10 should be resistant to and compatible with body fluids and medications. Additionally, when material selection is made for body 14 and latch member 44, the coefficient of sliding friction between the body and latch materials should be considered so that latch 44 is readily rotatable between the latched and the unlatched position. Additionally, since preferably, the adapter of the invention is supplied pre-sterilized to the practitioner, either as a separate item in a package or as a component in a procedure kit, the materials selected for adapter 10 should be compatible with the particular sterilization conditions selected.

Adapter 10 of the invention provides a practitioner with an easy-to-use adapter that is readily fitted onto a catheter tube. Proper placement of catheter tube 12 on the catheter seat is readily apparent to the practitioner through the viewing area and, because of the projections in the access port the catheter tube is less likely to fall out of the adapter of the invention before it is latched. Further, the invention provides the practitioner with positive indications that the adapter is ready to receive the catheter, when the catheter is properly positioned in the adapter and when the adapter is fully engaged to retain the catheter. The preferred elongate elliptical shape of the adapter of the invention is more easily handled by a gloved practitioner than the mostly cylindrical adapters currently available.

What is claimed is:

1. An adapter for attaching a fluid handling device to a catheter tubing comprising:

a body with a proximal end, a distal end and a passgaeway therethrough defining a longitudinal axis, said proximal end comprising a fitting for attaching a fluid handling device, said distal end of said body comprising an elongate receptacle having an inside surface with at least one engagement lug, an elongate resilient member disposed within said receptacle, said resilient member having a first end and a second end with a coaxial passage therethrough having an inside diameter to accept and to form a releasable substantially fluid tight connection to a preselected catheter tube with an outside diameter, said resilient member having a first conjugate engagement to said receptacle engagement lug at said first end and a second engagement at said second end;

a latch member disposed over said receptacle to contain said resilient member, said latch member having a distal axial access port therein for fitment of a proximal end of the catheter tube into said into said resilient member passage, said latch member having an inside surface with at least one second engagement lug for engaging said second end engagement of said resilient member, said latch member being disposed for rotatable movement with respect to said body between an insertion position wherein said passage in said resilient member is accessible to the catheter and said inside diameter of said resilient member passage is larger than the outside diameter of the catheter and a latched position wherein said inside diameter of said resilient member passage is smaller than the outside diameter of the catheter to retain the catheter in the receptacle; and wherein said rotation of said latch member with respect to said body between said insertion position and said latched position rotationally displaces said first end of said resilient member with respect to said second end of said resilient member thereby decreasing said inside diameter of said resilient member passage.

2. The adapter of claim 1 wherein said receptacle is generally coaxial with said passageway and is open distally with a closed bottom having a recess therein defining a catheter seat for fluidly connecting a lumen of the catheter to said proximal fitting.

3. The adapter of claim 2 wherein said adapter further comprises a substantially transparent viewing area.

4. The adapter of claim 3 wherein said substantially transparent viewing area of said body is formed into a shape to provide an enlarged image of said recess, thereby enhancing the practitioner's ability to properly place the catheter.

5. The adapter of claim 4 wherein said substantially transparent viewing area comprises a cylindrical lens shape thereby providing said enlarged image of said recess.

6. The adapter of claim 1 wherein said rotational movement of said latch with respect to said body is about one-quarter of a complete rotation.

7. The adapter of claim 6 further comprising indicator means for indicating said rotational position of said latch with respect to said body.

8. The adapter of claim 7 wherein said indicating means for indicating said position of said latch with respect to said body comprises said body and said latch each being formed in substantially similar asymmetric shapes so that when said latch is rotated to said latched position with respect to said body, said shapes are substantially aligned and when said latch is in said insertion position, said shapes are not substantially aligned thereby providing a visual and tactile indication of said position of said latch with respect to said body.

9. The adapter of claim 8 wherein said asymmetric shapes each comprises an elongate tube having substantially identical elliptical cross-sections, each shape having a long axis and a short axis, and disposed so that when said latch is in said latched position said long axes and said short axes are substantially aligned and when said latch is in said insertion position said short axis of said body is substantially aligned with said long axis of said latch, thereby providing said visual and tactile indication of the position of said latch with respect to said body and leverage to facilitate said rotatable movement of said latch with respect to said body.

10. The adapter of claim 1 wherein said first conjugate engagement at said first end of resilient member comprises three engagements for engaging three receptacle lugs and said second conjugate engagement at said second end of said resilient member comprises three engagements for engagement of three second lugs on said inside surface of said latch member.

11. The adapter of claim 1 wherein said resilient member is formed from a material selected from the group consisting of thermoform and thermoset elastomers.

12. The adapter of claim 11 wherein said thermoform and thermoset materials are selected from the group consisting of natural rubber, ethylene propylene dimer rubber (EPDM), styrene butadiene rubber (SBR), polyurethane elastomers and silastic rubber.

13. The adapter of claim 11 wherein said resilient member is formed from a latex free natural rubber having a Shore A durometer between about 30 and 80.

14. The adapter of claim 1 wherein said body and said latch member are formed from a thermoplastic material selected from the group consisting of polypropylene, polyethylene, polycarbonate and polystyrene.

15. The adapter of claim 1 wherein said fitting at said proximal end of said body comprises a female luer fitting.

16. The adapter of claim 15 wherein said fitting further comprises a removable cap.

17. The adapter of claim 1 wherein said distal access port further comprises an inside surface with at least one inward projection for retaining the catheter in said adapter prior to latching.

18. An adapter for attaching a fluid handling device to a catheter tubing comprising:

a body with a proximal end, a distal end and a passageway therethrough defining a longitudinal axis, said proximal end comprising a fitting for attaching a fluid handling device, said distal end of said body comprising an elongate receptacle having an inside surface with at least one engagement lug, an elongate resilient member disposed within said receptacle, said resilient member having a first end and a second end with a coaxial passage therethrough having an inside diameter to accept and to form a releasable substantially fluid tight connection to a preselected catheter tube with an outside diameter, said resilient member having a first conjugate engagement to said receptacle engagement lug at said first end and a second engagement at said second end;

a latch member disposed over said receptacle to contain said resilient member, said latch member having a distal axial access port therein for fitment of a proximal end of the catheter tube into said into said resilient member passage, said latch member having an inside surface with at least one second engagement lug for engaging said second end engagement of said resilient member, said latch member being disposed for about one-quarter of a complete rotation with respect to said body between an insertion position wherein said passage in said resilient member is accessible to the catheter and said inside diameter of said resilient member passage is larger than the outside diameter of the catheter and a latched position wherein said inside diameter of said resilient member passage is smaller than the outside diameter of the catheter to retain the catheter in the receptacle and wherein said adapter further comprises indicator means for indicating said rotational position of said latch with respect to said body, wherein said rotation of said latch member with respect to said body between said insertion position and said latched position rotationally displaces said first end of said resilient member with respect to said second end of said resilient member thereby decreasing said inside diameter of said resilient member passage.

* * * * *